US011491286B2

(12) United States Patent
Toksoz et al.

(10) Patent No.: US 11,491,286 B2
(45) Date of Patent: Nov. 8, 2022

(54) INHALER DEVICE WITH IMPROVED LOCKING CLIP (71) Applicant: ARVEN ILAC SANAYI VE TICARET A.S., Istanbul (TR)

(72) Inventors: Ahmet Toksoz, Istanbul (TR); Zafer Toksoz, Istanbul (TR)

(73) Assignee: ARVEN ILAC SANAYI VE TICARET A.S., Istanbul (TR)

( * ) Notice: Subject to any disclaimer, the term of this patent is extended or adjusted under 35 U.S.C. 154(b) by 551 days.

(21) Appl. No.: 16/348,134

(22) PCT Filed: Nov. 8, 2017

(86) PCT No.: PCT/EP2017/078635
§ 371 (c)(1),
(2) Date: May 7, 2019

(87) PCT Pub. No.: WO2018/087161
PCT Pub. Date: May 17, 2018

(65) Prior Publication Data
US 2019/0255263 A1 Aug. 22, 2019

(30) Foreign Application Priority Data

Nov. 9, 2016 (TR) .................................. 2016/16027
Dec. 22, 2016 (TR) .................................. 2016/19235

(51) Int. Cl.
*A61M 15/00* (2006.01)
(52) U.S. Cl.
CPC .... *A61M 15/0026* (2014.02); *A61M 15/0045* (2013.01); *A61M 15/0051* (2014.02); *A61M 15/0055* (2014.02); *A61M 2202/064* (2013.01)

(58) Field of Classification Search
CPC .......... A61M 15/0026; A61M 15/0051; A61M 15/0055; A61M 15/0045; A61M 15/0025; A61M 2202/064
See application file for complete search history.

(56) References Cited

U.S. PATENT DOCUMENTS

| 5,497,764 | A  | * | 3/1996 | Ritson | ................... | A61M 15/00 128/200.14 |
| 2007/0107720 | A1 | * | 5/2007 | Boeck | ................... | A61M 11/007 128/200.21 |
| 2009/0145431 | A1 | * | 6/2009 | Nobutani | ............. | A61M 15/025 128/203.12 |
| 2010/0089394 | A1 | * | 4/2010 | Sakurada | ............. | A61B 5/4839 128/203.14 |
| 2011/0209700 | A1 | * | 9/2011 | Kreutzmann | ..... | A61M 15/0021 128/200.14 |
| 2016/0193434 | A1 | * | 7/2016 | Gleixner | ........... | A61M 15/0066 128/200.16 |

* cited by examiner

*Primary Examiner* — Timothy A Stanis
(74) *Attorney, Agent, or Firm* — Kilpatrick Townsend & Stockton LLP (57) ABSTRACT

The present invention relates to a clip (2) that is disposed in the lock section of dry powder inhaler devices (1) and that has a beak-shaped first end (4) with a retaining tab (3) at the end thereof, a housing (9) through which a pin (11) connected to the device body (10) at the center section thereof passes, and a second tab (8) at a second end (7) thereof, wherein the second end (7) of said clip (2) is composed of two pieces, namely an upper piece (5) and a lower piece (6), and said pieces (5, 6) are joined at the beak-shaped first end (4).

5 Claims, 7 Drawing Sheets

INHALER DEVICE WITH IMPROVED LOCKING CLIP

CROSS-REFERENCE TO RELATED APPLICATIONS

This application is a National Phase Entry of PCT/EP2017/078635, filed Nov. 8, 2017, which claims the benefit of priority to TR Patent Application No. 2016/16027, filed Nov. 9, 2016, and TR Patent Application No. 2016/19235, the teachings of which are hereby incorporated by reference in their entireties for all purposes.

TECHNICAL FIELD

The present invention relates to a device providing the administration of dry powder inhalation medicament. The present invention particularly relates to advancements in the locking clip structure of dry powder inhaler devices.

PRIOR ART

Despite the advances in diagnosis and treatment in recent years, diseases such as asthma, bronchitis and COPD (Chronic Obstructive Pulmonary Disease) decrease the quality of life of humans. The administration of medicaments by means of inhalers is recommended for optimizing the treatment of these types of diseases. The treatment by means of inhalers is the most preferred treatment type and is expected to be the first option in the future. The most important advantage of using medicaments by means of inhalation is to provide a more efficient treatment by using less medicaments, to administer medicaments in a higher concentration the respiratory tract and in particular to decrease the systemic side effects of medicaments. Despite the presence of very efficient treatments for respiratory tract diseases, the most significant reasons of failing to properly control patients are stated as noncompliance with the treatments recommended by the physicians and incoordination due to the improper use of inhalers.

In recent years, various inhalation devices have been developed for administering inhalation medicaments. These devices are basically categorized into two types: metered-dose inhalers and dry powder inhalers. These types of devices structurally comprise basic components such as mechanism, counter, body, lid, lock, etc. In addition, powder inhalation medicaments are preserved in carriers such as blister, capsule, etc. Blisters are composed of two basic components, namely the main layer with cavities for carrying the medicament and the strippable lid layer.

The type of dry powder inhaler devices with blisters comprises a mechanism that moves the blister forward and provides the sequential use of cavities in the blister. The patient uses an arm or a trigger to move said mechanism. This type of devices has main components such as advancement mechanism, counter and lock and mechanism that form the same.

In the state of the art inhaler devices, various types of locks providing the operational safety are used. In patents no. EP2239001 B1 and EP2239002B1, locking mechanisms used in inhaler devices are disclosed.

The locking mechanism of the blister inhaler devices disclosed in the state of the art patents operates in the following manner.

Following the opening of the lid of the device, the user applies force onto the pushing member. Afterwards, the pushing member is guided by means of the rails in the body and on the pushing member itself so as to be slid into the housing section. The linear gear disposed at the upper section of the pushing member transmits this movement to other gears, thus providing the operation of the mechanism. As a result of the sliding of the pushing member into the outer body, the tab retaining housing arranged on the pushing member fixedly engages with the beak-shaped locking clip front locking tab disposed right thereabove, providing the administration of the single dose medicament by means of the mouthpiece. As the user continues to make the pushing movement until said locking position, the blister is enabled to be completely stripped and the proper administration of required dose of medicament is assured. As a result of said locking, the pushing member is fixed and is deactivated for a short period. Moreover, said pushing movement causes the helical spring to be compressed between the inner section of the outer body and the pushing member. After the user closes the lid following the use of the powder medicament, the pressing surface at the end portion of the lid applies pressure onto the rear section of the locking clip and lifts the end, thus separating the clip front tab and the tab retaining housing from each other. Consequently, the compressed spring pushes the pushing member backwards and the device becomes ready for use without the need for the user to wind up the same. When the housing of the pushing member, which moves up to the backmost position possible, is aligned with the clip rear locking tab, the housing and the tab engage with each other. Thus, the pushing member is locked at the backmost position thereof. This operation is realized by means of a single-piece clip. In light of the description given herein, it is clear that the device can be used only with a single pushing movement by the user. With the closing of the lid, the device is automatically wound up and the device becomes ready for reuse. During the rewinding operation when said device becomes ready for reuse, a problem is encountered in bringing the pushing member to the pushing position. When closed, the lid of the device applies pressure to the rear side of the beak-shaped clip, the front end is lifted up like a seesaw by means of the pin passing through the housing at the center thereof, and thus, the pushing member moves backwards with the effect of the compressed spring. However, since the single-piece rear end/section of the clip is squeezed from above by the lid of the device during this operation, said pushing member rubs against the clip and cannot be easily moved backwards/brought to the wind-up position, and is jammed. This jamming causes the breaking and wearing of the pushing member and of the clip. Moreover, if the pressure is higher, the locking in the reuse position cannot be properly realized.

Consequently, in the relevant technical field, an efficient, low-cost and practical novelty providing operation with the desired precision and usage advantages is required in order to eliminate said problems in the inhaler devices.

AIMS AND BRIEF DESCRIPTION OF THE INVENTION

The present invention relates to an improved inhaler device and lock used in dry powder inhalation operation, that eliminate all the above-mentioned problems and that provide advantages to the relevant technical field.

With respect to the state of the art, the principal aim of the present invention is to provide a dry powder inhaler device that operates with the desired precision, that enables the blisters to be stripped and used and that realizes this operation in an error-free manner with respect to the precedent devices.

Another aim of the present invention is to provide an inhaler device assembly providing that each medicament-carrying blister cavity about to be used can be properly stripped by means of a locking mechanism having a pushing member that can move in a predetermined movement distance.

Yet another aim of the present invention is to prevent the inhaler device from being used involuntarily by means a clip that is disposed in the device and that enables the same to be locked in the positions where the device is ready for use and the lid thereof is closed.

Yet another aim of the present invention is to reduce the pressing force required to be applied onto the trigger of the device and the spring force required for automatic rewinding in order to provide the operation of said device.

Yet another embodiment of the present invention is to prevent breaking and wearing by reducing the contact force between the trigger/pushing member and the locking clip.

In order to attain all the aims that are described above and that may arise from the below detailed description, a novelty is developed at the clip that is disposed in the lock section of the dry powder inhaler devices and that has a beak-shaped first end with a retaining tab at the end thereof, a housing through which a pin connected to the device body at the center section thereof passes, and a second tab at the second end thereof.

In a preferred embodiment of the present invention, said novelty is realized by providing the second end of said clip as a two-piece component, namely an upper piece and a lower piece and by joining said pieces at the beak-shaped first end.

In a preferred embodiment of the present invention, said upper and lower pieces move independently of each other.

In a preferred embodiment of the present invention, said upper and lower pieces are angularly positioned with respect to each other.

In a preferred embodiment of the present invention, said upper and lower pieces are positioned parallel to each other.

In a preferred embodiment of the present invention, said upper and lower pieces are flexible.

REFERENCE NUMBERS IN FIGURES

1. Inhaler device
2. Clip
2.1 Clip spring
3. Clip first end retaining tab
4. Clip first end
5. Clip second end upper piece
6. Clip second end lower piece
7. Clip second end
8. Clip second end retaining tab
9. Housing
10. Outer body
11. Pin
12. Mouthpiece
13. Lid
14. Blister cavity
15. Blister
16. Guide gear housing
17. Guide gear
18. Inner body
19. Lower housing
20. Left center housing
21. Right center housing
22. Upper housing
23. Upper rolling gear of the blister lid
24. Intermediate rolling gear of the blister lid
25. Lower rolling gear of the blister lid
26. Trigger
27. Spring
28. Receptacle
29. Drive plate
30. Transmission gear
31. First additional gear
32. Second additional gear
33. Housing

DETAILED DESCRIPTION OF THE INVENTION

A clip (2) that is disposed in the lock section of the inhaler device (1) of the present invention is explicated in an exemplary manner referring to the attached figures only so as to clarify without introducing any limiting effects.

Figure 3:
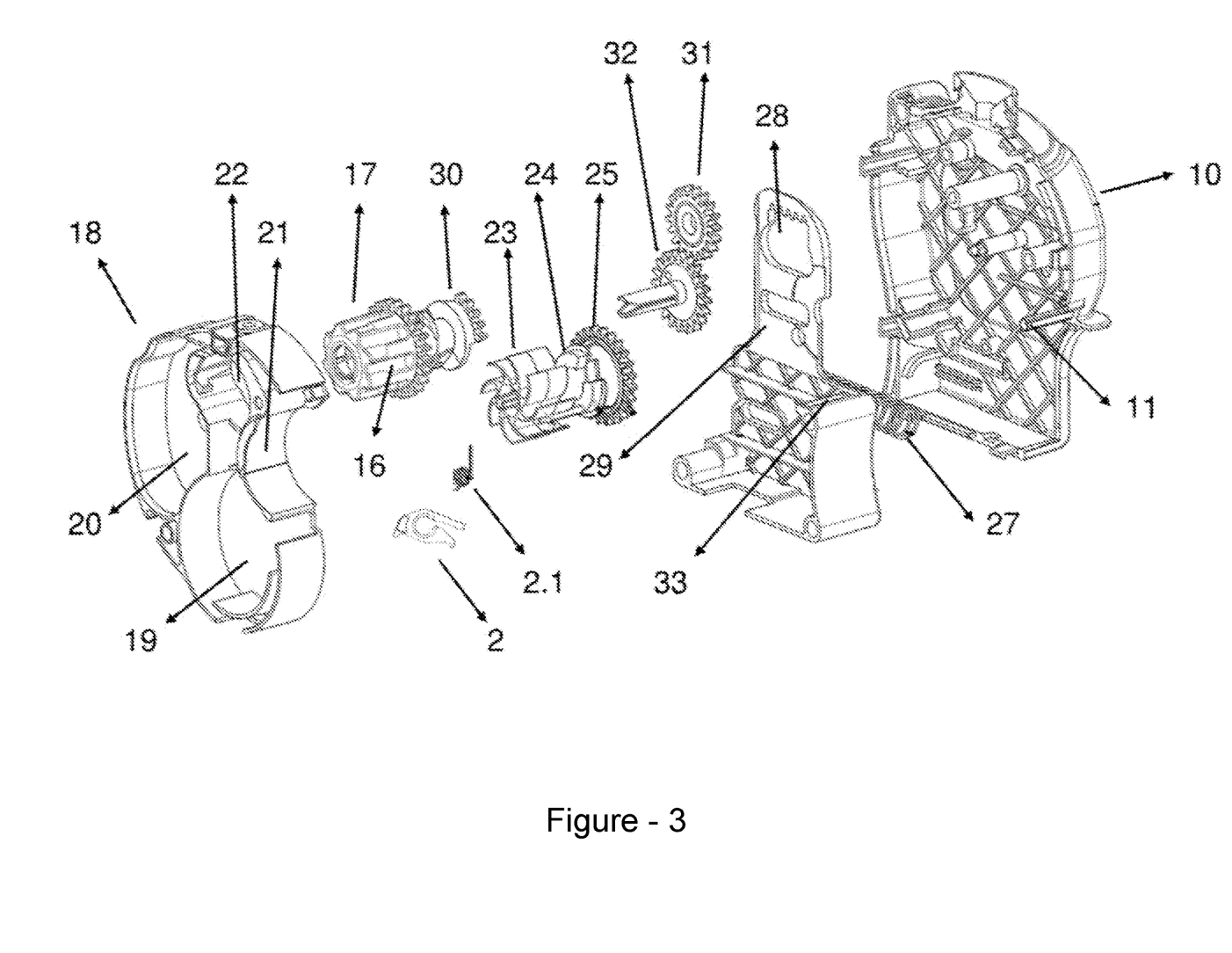
FIG. 3 shows the representative perspective view of the inhaler device of the present invention in the disassembled state.
Figure 5:
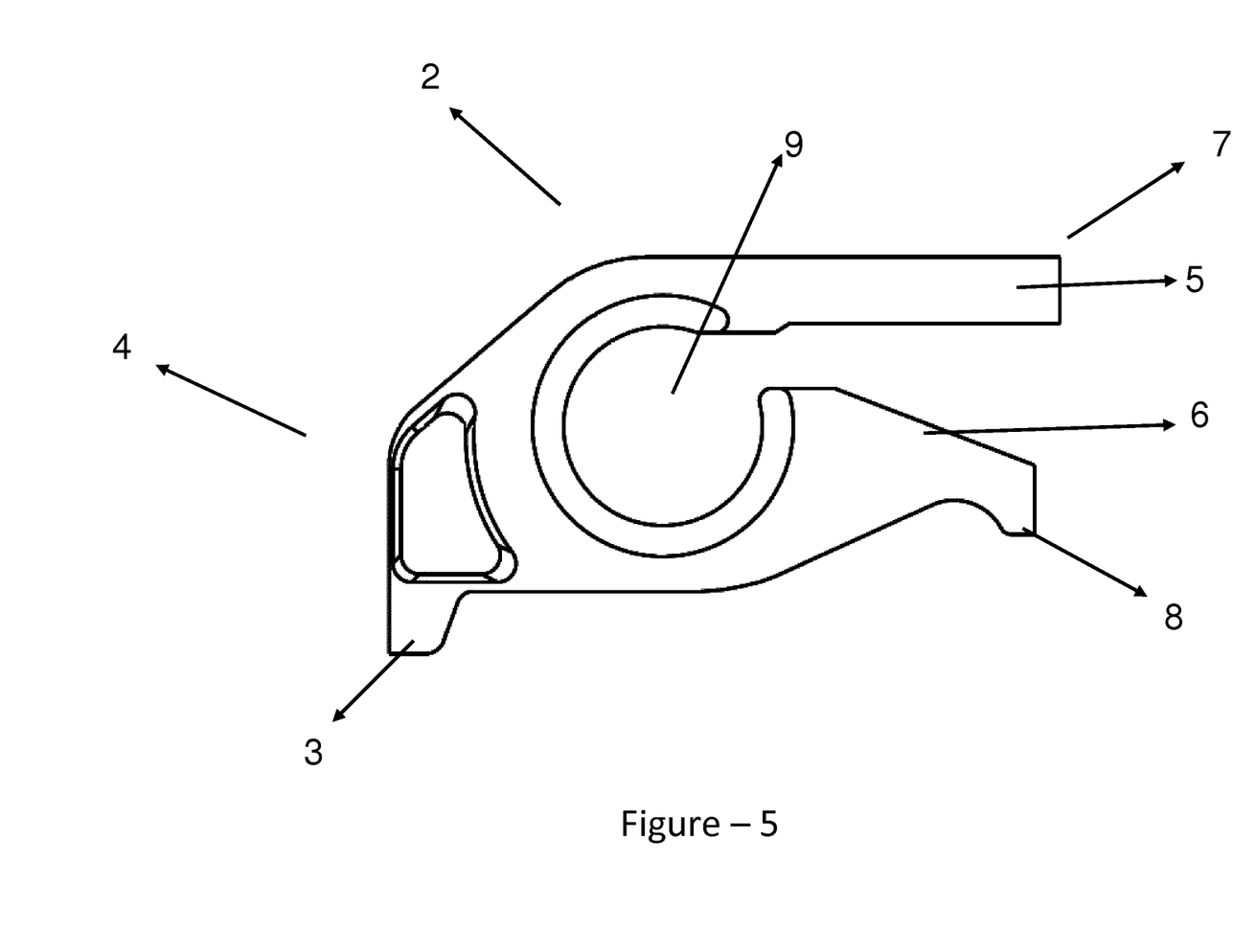
FIG. 5 shows the detailed perspective view of the clip disposed in the inhaler device of the present invention.
Figure 6:
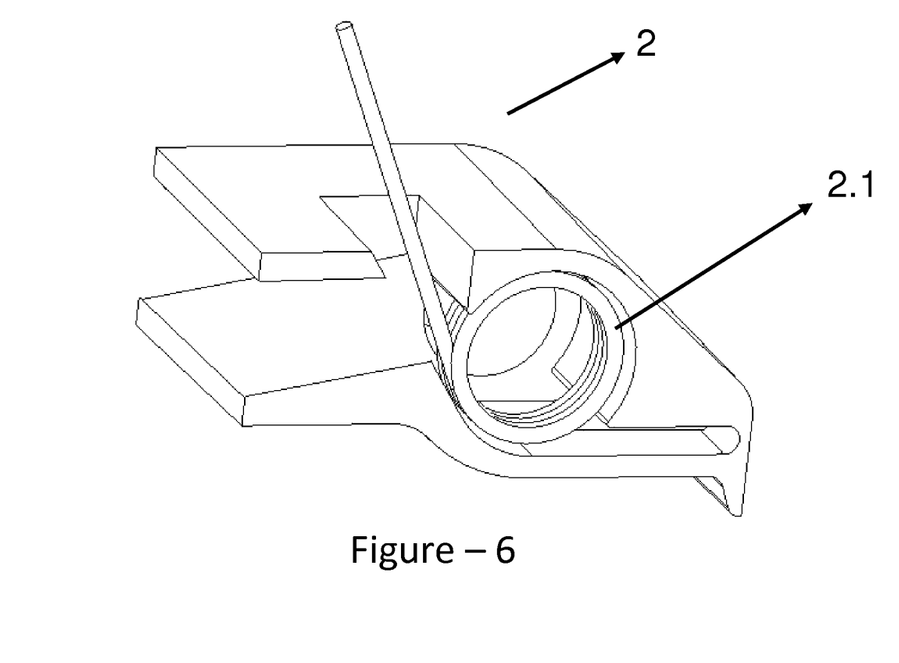
FIG. 6 shows the detailed perspective view of the clip disposed in the inhaler device of the present invention.

The clip (2) of which the representative view is given in FIGS. 3, 5 and 6 is composed of a beak-shaped first end (4) having a retaining tab (3) and a second end (7) formed by two planar pieces, namely an upper piece (5) and a lower piece (6). A second retaining tab (8) is provided at the extension of the lower piece (6) of the second end (7). Moreover, a housing (9) is provided at the center of said second end (7). Said housing (9) in the clip (2) is connected to a pin (11) in the body (10) of the inhaler device (1). The connection between said housing (9) and the pin (11) enables said clip (2) to freely rotate. Said rotational movement is realized upwards and downwards in a limited manner. A spring (2.1) controls the limited rotation of the clip (2) and assures the stable position thereof in the horizontal axis. Said spring (2.1) is of helical type with one end, which constitutes the extension thereof, being linear. The helical section of the spring (2.1) is positioned in a housing formed in the body of the clip (2) while the linear section thereof is positioned in a housing formed at the inner edge surface of the outer body (10). Thus, the linear section of said spring (2.1) is fixed in the housing at the inner edge surface of the outer body (10) so as to limit the rotational movement while the helical section in the clip (2) provides the free rotation.

Figure 1:
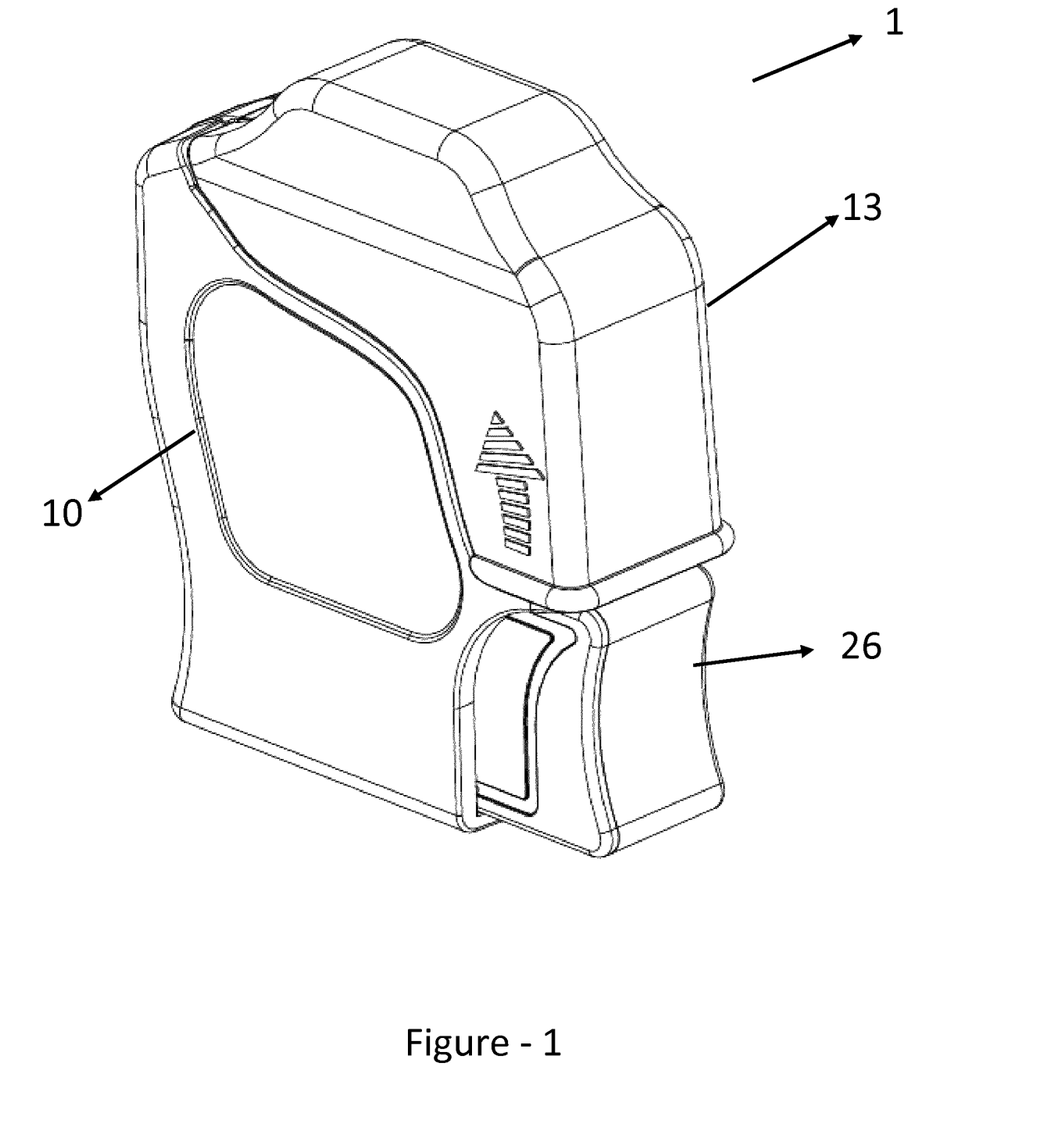
FIG. 1 shows the perspective view of a representative embodiment of the inhaler device of the present invention.
Figure 2:
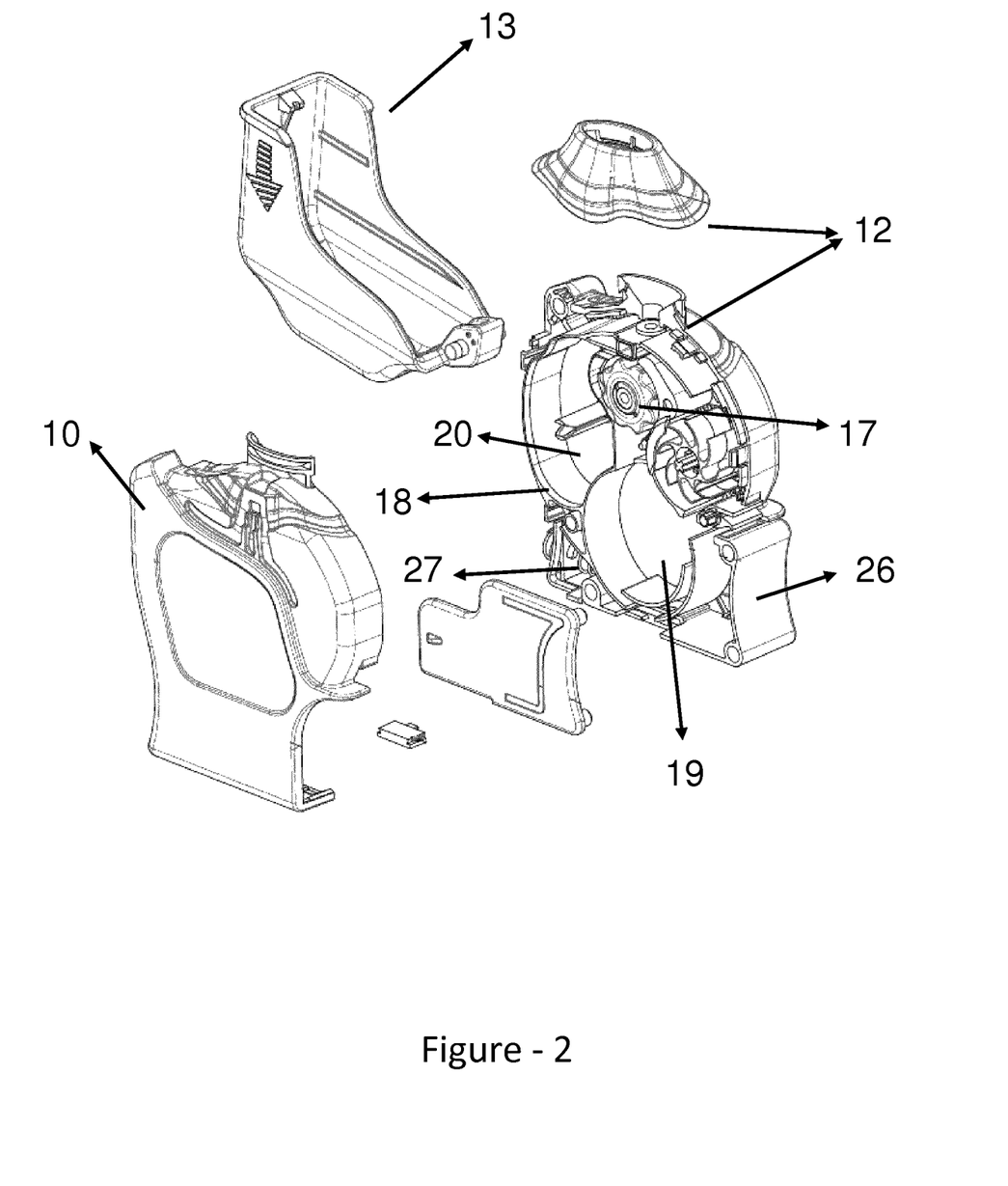
FIG. 2 shows the representative perspective view of the inhaler device of the present invention in the disassembled state.

The outer body (10) of the inhaler device (1) of the present invention of which the representative view is given in FIGS. 1, 2 and 3 is composed of two compatible parts with retaining tabs disposed thereon. Surface protrusions extending in the horizontal and vertical directions are provided at the inner section of said parts so as to form a frame supporting the body. The outer body (10) is formed by mounting said two parts to each other. A mouthpiece (12) enabling the user to inhale a medicament is provided at the upper part of said outer body (10). The mouthpiece (12) is composed of two parts, namely a section as an extension of the outer body (10) and an attachable/detachable headpiece. In order to keep the mouthpiece (12) clean and prevent foreign bodies from entering the inhaler device (1) when said inhaler device (1) is not being used, a lid (13) that pivots on the outer body (10) and that is closed on the mouthpiece (12) is provided.

According to the representative views given in FIGS. 2, 3, 4 and 7, a blister (15) advancement mechanism gear group is disposed at the inner section of the outer body (10) so as to provide the operation of the inhaler device (1). A blister (15) having cavities (14) filled with powder medicaments is positioned along the intermediate channels of said gear group. In said gear group, just under the mouthpiece (12), a guide gear (17) is provided, wherein the blister (15) cavities (14) filled with powder medicaments are disposed into housings (16) arranged on the body of the guide gear (17). The housings (16) of the guide gear (17) are positioned right under the mouthpiece (12) of the device (1). An inner body (18) of which the representative view is given in FIGS. 2 and 3 is provided at the inner section of the outer body (10) so as to provide the positioning of the blister (15). The inner body (18) has a single-piece structure with all the lateral sides thereof being closed walls and allows the positioning of the blister (15) advancement mechanism gear group and of the blister (15). Said single-piece inner body (18) comprises a lower housing (19), a left center housing (20), a right center housing (21), an upper housing (22), recessed surfaces and tabs. The unused, full blister (15) is stored in the lower housing (19) and said strip-shaped blister (15) extends along the intermediate channels so as to be divided into two parts, namely the main layer and the lid layer, by means of the mechanism. The main layer of the blister (15) divided into two is rolled into the left center housing (20) and the lid layer thereof is rolled over a blister (15) lid upper rolling gear (23) that is positioned in the right center housing (21).

Figure 4:
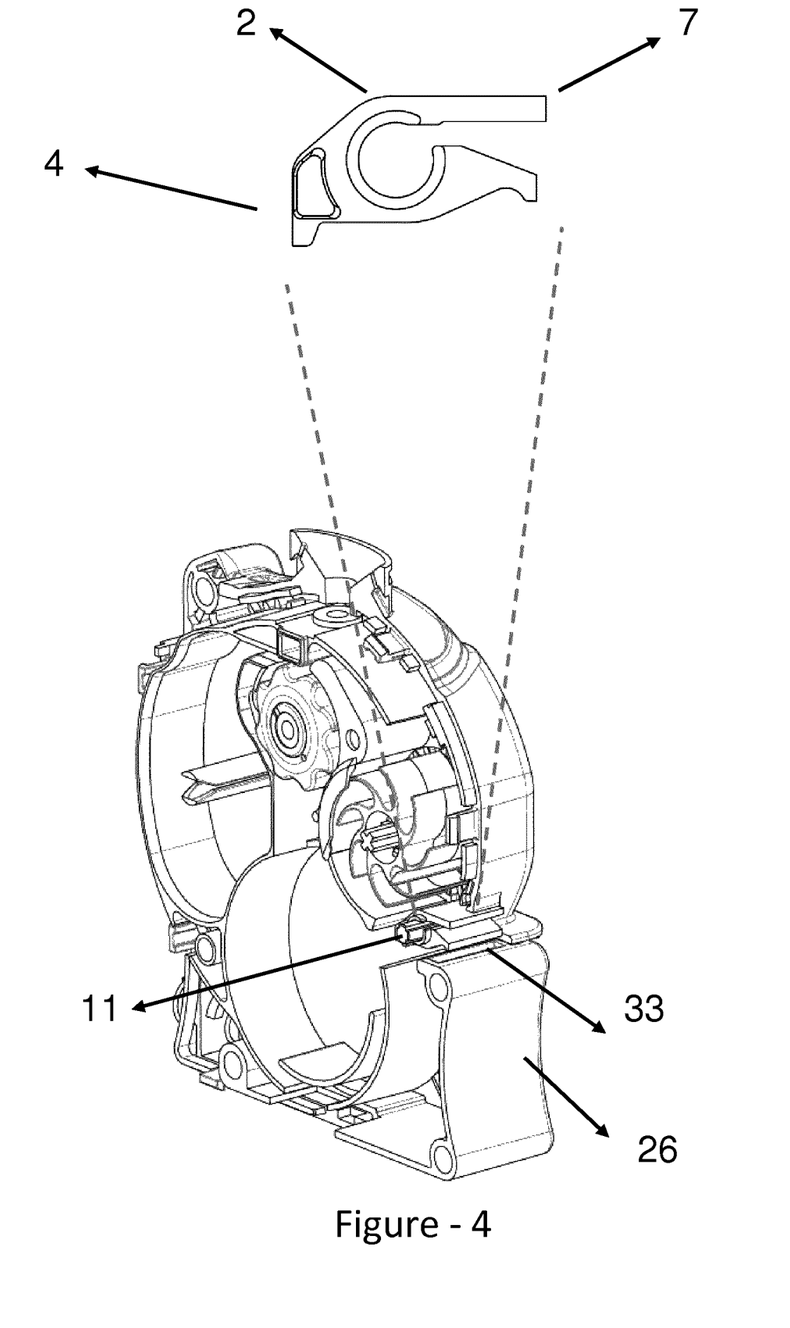
FIG. 4 shows the detailed perspective view of the clip disposed in the inhaler device of the present invention.

At the beginning of the blister (15) advancement mechanism gear group of which the representative views are given in FIGS. 2, 3 and 4, a trigger (26) is provided, that is slidably disposed at the lower part of the outer body (10). Said trigger (26) can move in the axial/linear direction at the inner section of the outer body (10). The surface on the outer section of the trigger (26) on which the user applies pressure to push said trigger (26) inwards has a concave structure so as to provide ease of use. Between said trigger (26) and the inner surface of the outer body (10) a spring (27) is provided, that is compressed (loaded) when said trigger (26) is pushed into the outer body (10). Said spring (27) has a helical form.

In the inhaler device (1) of the present invention, a drive plate (29) is provided, that is fixed to said trigger (26) from one end and that has a receptacle (28) at the other end thereof. Said receptacle (28) is formed so as to be large enough to receive a gear therein. In the receptacle (28) of said drive plate (29), linear gears are provided, that are arranged in the axial/linear direction wherein the trigger (26) moves. The receptacle (28) is preferably rectangular and said gears are arranged at the upper edge of the receptacle (28). A transmission gear (30) is positioned in said receptacle (28). The transmission gear (30) is movably connected from the center thereof to a pin fixed to the inner body (18). Said connection allows the transmission gear (30) to make only rotational movement. A portion of the base peripheral surface of the transmission gear (30) contains teeth while the remaining portion does not have any teeth. The teeth of the transmission gear (30) engage with the linear gear of the drive plate (29). The surface of the transmission gear (30) comprising teeth in engagement with the linear gear realizes the rotation function. The surface portion without any teeth rotates inside the receptacle (28) without contacting any surfaces, thus providing an advantage in the volume and enabling the volume of the receptacle (28) to be in the acceptable range. Said transmission gear (30) engages with the guide gear (17). The guide gear (17) engages with the transmission gear (30) so as to identically imitate the movement of the transmission gear (30).

In light of the detailed description above, the inhaler device (1) of the present invention operates in the following manner. After the opening of the lid (13), the user applies force onto the gripping surface of the trigger (26). Afterwards the trigger (26) is slid into the outer body (10). With the axial/linear movement of said trigger (26), the drive plate (29) in connection with the trigger (26) is also slid. Thus, the transmission gear (30) in engagement with the linear gear of the drive plate (29) makes rotational movement. With the movement of the transmission gear (30), the guide gear (17) disposed thereon starts rotating and rotates the gears with which the guide gear (17) engages. Thus, the blister (15) positioned on the gears is moved and said blister (15) cavities (14) are opened.

Figure 7:
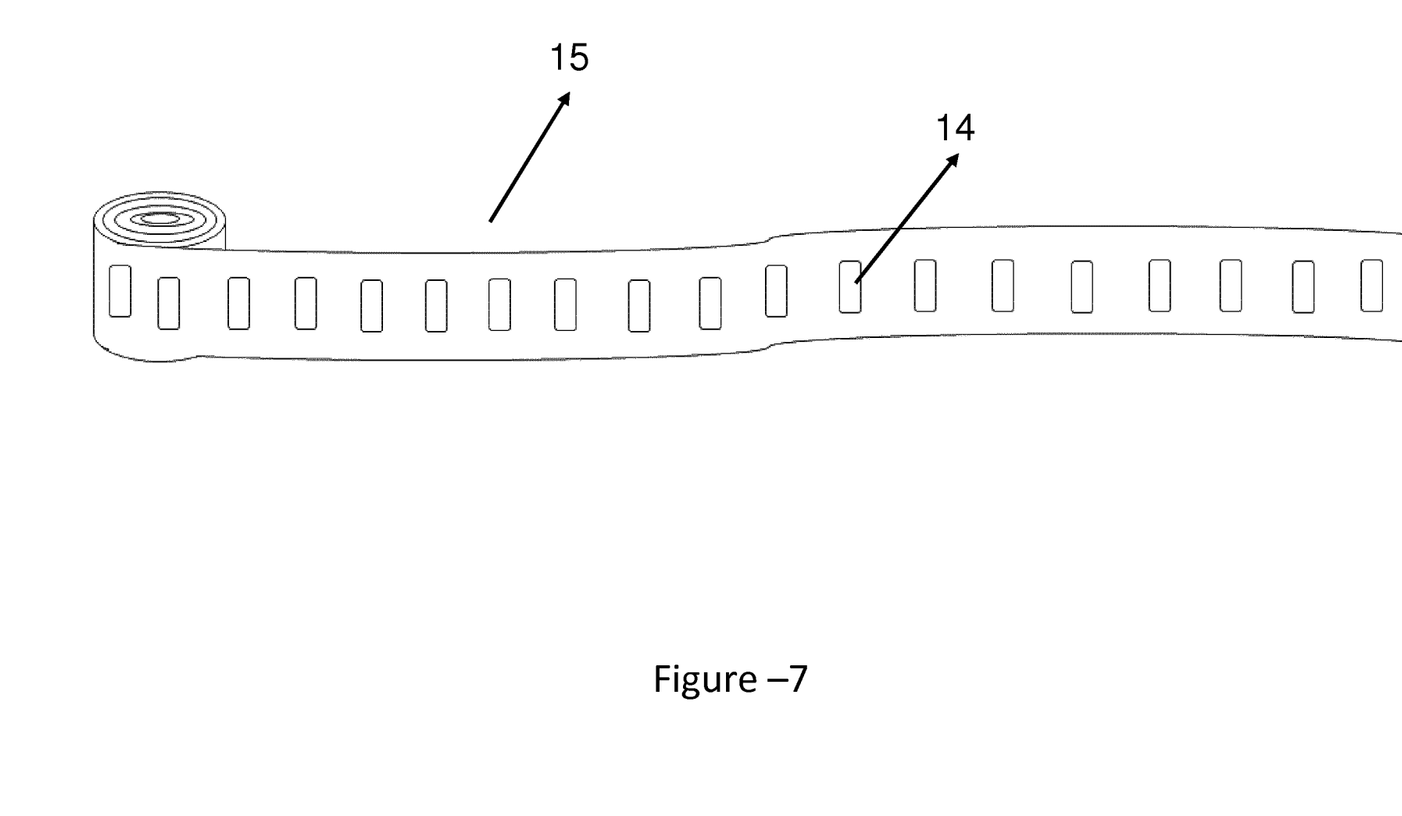
FIG. 7 shows the view of a representative embodiment of the blister disposed in the inhaler device of the present invention.

The guide gear (17) of which the representative embodiment is shown in FIGS. 2, 3 and 7 moves unidirectionally and realizes only the forward movement of the blister (15). The transmission gear (30) in engagement with the guide gear (17) can rotate forwards or backwards. By means of the guide gear (17), the transmission gear (30) transmits this movement to a first additional gear (31) and a second additional gear (32) as well as to the upper rolling gear (23), the intermediate rolling gear (24) and the lower rolling gear (25) of the blister (15) lid which engage with each other. While the transmission gear (30) and the guide gear (17) rotate counterclockwise, the lower rolling gear (25) of the blister (15) lid and the intermediate rolling gear (24) and the upper rolling gear (23) of the blister (15) lid which are positioned thereabove rotate clockwise. The blister (15) in engagement with said gears (23, 24, 25) moves through the channels of the inner body (18) and is stripped while passing through the blister (15) mechanism gear groups, thus the medicament in the blister (15) cavity (14) is exposed. The main layer of the blister (15) divided into two is rolled into the left center housing (20) and the lid layer thereof is rolled over the blister (15) lid upper rolling gear (23) that is positioned in the right center housing (21).

As a result of the trigger (26) being slid into the outer body (10), a housing (33) arranged on the trigger (26) fixedly engages with the locking clip (2) tab (3) positioned right thereabove, thus providing the use of a single dose of medicament. As the user continues to make the pushing movement until said locking position, the blister (15) is enabled to be completely stripped and the proper administration of required dose of medicament is assured. As a result of said locking, the trigger (26) is fixed and the pushing member is deactivated for a short period. Moreover, said pushing movement causes the spring (27) to be compressed between the inner surface of the outer body (10) and the trigger (26).

After the user closes the lid (13) following the use of the powder medicament, the lid (13) applies pressure onto the second end (7) of the locking clip (2) and lifts the first end (4), thus separating the tab (3) of the first end (4) of the clip (2) and the retaining housing (33) at the upper side of the trigger (26) from each other. Here, the advantage of the embodiment of the present invention becomes evident. The second end (7) of said clip (2) is composed of two planar pieces moving independently of each other, namely the upper piece (5) and the lower piece (6), and said pieces (5, 6) are joined at the first end (4). By means of this independently moving structure, the upper piece (5) on which the lid (13) applies pressure from above enables the clip (2) to move around the pin (11) like a seesaw. The first end (4) is lifted as the edge of the lid (13) applies pressure on the upper piece (5) of the second end (7) of the clip (2). Thus, the retaining tab (3) of the clip (2) locked in the housing (33) of the trigger (26) is freed and the trigger (26) is slid backwards by means of the compressed/loaded spring (27). At the same time, the lower piece (6) of the second end (7) of the clip (2) can move freely although being in contact with the upper surface of the slid trigger (26), the lower piece (6) stretches so as to allow the trigger (26) to be slid/moved backwards. Thus, the trigger (26) reaches to the exact pressing position. The upper piece (5) and the lower piece (6) that stretch independently of each other at the second end (7) of the clip (2) enable the trigger (26) to move even with a very low force applied by the user. Similarly, a very low spring (27) force is required to slide the trigger (26) backwards so as to make the device (1) ready for use.

As the trigger (26) is slid backwards, the mechanism rotates the transmission gear (30) in the reverse direction, thus providing the reverse movement of the mechanism. Thus, the device (1) becomes ready for reuse without the need for the user to wind up the same. However, the mechanism cannot move the blister (15) in the reverse direction. In light of the description given herein, it is clear that the inhaler device (1) of the present invention can be used only with a single pushing movement by the user. With the closing of the lid (13), the device (1) is automatically wound up and the device (1) becomes ready for reuse.

The linear movement of the trigger (26) is realized as the trigger (26) being slid in any direction including the x and y axes. Said direction is determined according to the design of the device (1).

The term "blister (15) advancement mechanism gear group" comprises the guide gear (17), the transmission gear (30), the blister (15) lid lower rolling gear (25), the blister (15) lid intermediate rolling gear (24), the blister (15) lid upper rolling gear (23), the first additional gear (31) and the second additional gear (32), and other wheels and gears that can be added to the main components of the device (1) are considered within the scope of this term.

Consequently, by means of the described embodiment, an inhaler device (1) having a highly precise and smoothly operating mechanism is realized.

The invention claimed is:

1. A dry powder inhaler device comprising a clip that is disposed in a lock section of the dry powder inhaler device and that has a beak-shaped first end with a retaining tab at an end thereof, a housing through which a pin connected to a device body at a center section thereof passes, and a second tab at a second end of the clip, characterized in that the second end of said clip is composed of two pieces, namely an upper piece and a lower piece, and said pieces are joined at the beak-shaped first end.

2. The dry powder inhaler device as in claim 1, characterized in that said upper piece and said lower piece move independently of each other.

3. The dry powder inhaler device as in claim 1, characterized in that said upper piece and lower piece are angularly positioned with respect to each other.

4. The dry powder inhaler device as in claim 1, characterized in that said upper piece and lower piece are positioned parallel to each other.

5. The dry powder inhaler device as in claim 1, characterized in that said upper piece and lower piece are flexible.

* * * * *